(12) United States Patent
Kida et al.

(10) Patent No.: US 8,896,826 B2
(45) Date of Patent: Nov. 25, 2014

(54) INSPECTION SYSTEM FOR COATED PAPER

(71) Applicant: Japan Tobacco Inc., Tokyo (JP)

(72) Inventors: Shinzo Kida, Tokyo (JP); Masaaki Fukaya, Tokyo (JP); Takafumi Izumiya, Tokyo (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 13/871,674

(22) Filed: Apr. 26, 2013

(65) Prior Publication Data
US 2013/0242292 A1 Sep. 19, 2013

Related U.S. Application Data

(63) Continuation of application No. PCT/JP2010/069332, filed on Oct. 29, 2010.

(51) Int. Cl.
| | | |
|---|---|---|
| *G01N 21/00* | (2006.01) | |
| *G01N 21/89* | (2006.01) | |
| *A24C 5/00* | (2006.01) | |
| *D21H 23/78* | (2006.01) | |
| *G01N 21/952* | (2006.01) | |
| *A24C 5/34* | (2006.01) | |
| *G01N 21/88* | (2006.01) | |
| *D21H 23/22* | (2006.01) | |

(52) U.S. Cl.
CPC ........ *G01N 21/952* (2013.01); *G01N 2021/888* (2013.01); *G01N 21/8901* (2013.01); *A24C 5/005* (2013.01); *G01N 2021/8917* (2013.01); *D21H 23/78* (2013.01); *G01N 2021/8861* (2013.01); *D21H 23/22* (2013.01); *A24C 5/3412* (2013.01)
USPC ..................................... 356/237.2; 356/237.1

(58) Field of Classification Search
CPC ...... A24C 5/005; A24C 5/3412; D21H 23/22; D21H 23/78; G01N 2021/8861; G01N 2021/888; G01N 2021/8917; G01N 21/59; G01N 21/8901; G01N 21/952
USPC ........................... 356/237.1–237.6, 429–431, 356/239.3–239.7; 131/284, 905, 280, 908; 162/198
See application file for complete search history.

(56) References Cited

U.S. PATENT DOCUMENTS 6,020,969 A    2/2000 Struckhoff et al.
6,198,537 B1 *  3/2001 Bokelman et al. ............ 356/429
(Continued)

FOREIGN PATENT DOCUMENTS

JP    2001-509366 A    7/2001
JP    2001-509598 A    7/2001
(Continued)

*Primary Examiner* — Tri T Ton
(74) *Attorney, Agent, or Firm* — Birch, Stewart, Kolasch & Birch, LLP

(57) ABSTRACT

An inspection system for coated paper includes a traveling web of paper, a coating device for forming bands on the web by applying a coating liquid in the width direction of the web such that the bands are spaced from each other in the longitudinal direction of the web at regular intervals, a drying device for drying the web having the bands, a detection unit which is arranged downstream of the coating device for detecting at least either defect in the bands or defect in the web that is caused due to application of the coating liquid. A control device is inputted with the detection result from the detection unit and includes a determination section for determining the type of defect from the detection result. A quality control unit is inputted with the determination result from the determination section and configured to manage the determination result.

14 Claims, 4 Drawing Sheets

(56) References Cited

U.S. PATENT DOCUMENTS

| | | |
|---|---|---|
| 2005/0229941 A1 | 10/2005 | Minami et al. |
| 2005/0252516 A1 | 11/2005 | Izumiya et al. |

FOREIGN PATENT DOCUMENTS

| | | |
|---|---|---|
| JP | 2005-214875 A | 8/2005 |
| JP | 2006-292678 A | 10/2006 |
| JP | 2008-534795 A | 8/2008 |
| JP | 4201767 B2 | 12/2008 |
| JP | 2009-148759 A | 7/2009 |
| WO | WO 02/44700 A1 | 6/2002 |
| WO | WO 2004/056220 A1 | 7/2004 |
| WO | WO 2004/064546 A1 | 8/2004 |
| WO | WO 2006/100607 A2 | 9/2006 |

* cited by examiner

INSPECTION SYSTEM FOR COATED PAPER

This application is a Continuation of PCT/JP2010/069332 filed Oct. 29, 2010, the contents of which are hereby expressly incorporated by reference into the present application.

TECHNICAL FIELD

The present invention relates to an inspection system for inspecting the quality of coated paper.

BACKGROUND ART

Low-ignition-propensity wrapping paper for use in cigarettes has recently been known as a kind of coated paper. When a cigarette formed using such low-ignition-propensity wrapping paper is lit at one end, the cigarette burns at a low rate of spread toward the other cigarette end. Specifically, the low-ignition-propensity wrapping paper is obtained by applying a combustion inhibitor in liquid form to a web of paper such that the inhibitor-applied regions (bands) extend in the width direction of the web and are spaced from each other in the longitudinal direction of the web at predetermined intervals, and then drying the web.

An inspection apparatus has been known which is configured to inspect the width and spacing of regions applied with a coating liquid as exemplified by the above combustion inhibitor, in the process of manufacturing wrapping paper for cigarettes (Patent Document 1). Also, there has been known a cigarette paper manufacturing machine in which the width of bands formed by applying a coating liquid to a web is inspected by an inspection apparatus and the amount of a combustion inhibitor applied as the coating liquid to form the bands is adjusted (Patent Document 2).

PRIOR ART DOCUMENTS

Patent Documents

Patent Document 1: PCT International Application-based Japanese Unexamined Patent Publication No. 2001-509366
Patent Document 2: Japanese Unexamined Patent Publication No. 2009-148759

SUMMARY OF THE INVENTION

Problems to be Solved by the Invention

The aforementioned inspection apparatuses are capable of measuring the width and spacing of bands. However, where there is a defect in the bands, for example, if part of a band is missing, such a defect cannot be detected by the inspection apparatuses. Also, where a defect occurs in the web due to formation of the bands, that is, if the web is partly torn or the surface of the web is stained, such defects also cannot be detected by the inspection apparatuses. In cases where such defects have occurred in the web, portions of the web containing the defects should desirably be removed so that the defective portions may not be used as the wrapping paper for cigarettes, namely, as the coated paper.

The present invention provides an inspection system for coated paper, which system is capable of reliably detecting defects in bands of the coated paper as well as defects in a web caused by formation of the bands, and also can reliably identify portions of the web containing such defects, thereby enabling improvement in the productivity of the coated paper.

Means for Solving the Problems

According to the present invention, there is provided an inspection system for coated paper, including: a traveling path along which a web of paper travels; a coating device configured to form a plurality of bands on the web by applying a coating liquid in a width direction of the web such that the bands are spaced from each other in a longitudinal direction of the web at regular intervals; a drying device configured to dry the web having the bands formed thereon; a detection unit arranged downstream of the coating device and configured to detect at least either defect in any one of the bands or defect in the web that is caused due to application of the coating liquid to the web; a control device input with a detection result from the detection unit and including a determination section configured to determine a type of the defect from the detection result; and a quality control unit input with a determination result from the determination section and configured to manage the determination result.

Preferably, the determination section determines whether the defect of the band is a severe one or a minor one.

Preferably, the quality control unit includes a storage section configured to store the determination result.

Preferably, the determination section determines a position of the defect of the band or the web with respect to the web and outputs a determination result to the storage section, and the quality control unit further includes a marking device arranged downstream of the drying device and configured to affix, on the web, a mark indicative of presence of the defect of the band or the web in accordance with the position of the defect stored in the storage section.

Preferably, the detection unit includes a first detection device arranged upstream of the drying device and configured to detect defect in any one of the bands, the first detection device includes a sensor configured to detect presence and absence of each of the bands and a rotary encoder configured to output a signal at every inspection time when each of the bands is to pass the sensor, and the determination section judges that a severe defect has occurred if it is found based on outputs from the sensor and the rotary encoder that the bands are not formed at the regular intervals.

Preferably, the determination section includes a counter circuit configured to count pulses output from the rotary encoder, and in this case, the determination section stores, in advance as a reference pulse count, a number of the pulses to be counted between adjacent ones of the bands, and judges that the bands are not formed at the regular intervals if the reference pulse count is exceeded by a number of actually counted pulses.

Preferably, the control device further includes a stop signal sending section configured to output an instruction to stop traveling of the web when it is judged by the determination section that the severe defect has occurred.

Preferably, the first detection device further includes a first camera configured to image the web having the bands formed thereon, and a first image processor configured to detect defect in any one of the bands from an image acquired by the first camera.

Preferably, the defect of the band detected by the first image processor includes stain, uneven coating and pinhole that appear at random, periodically or continuously.

Preferably, the detection unit includes a second detection device arranged downstream of the drying device and upstream of the marking device and configured to detect defect in the web, and the determination section is input with a detection result from the second detection device.

Preferably, the second detection device includes a second camera configured to image the web, and a second image processor configured to detect defect in the web from an image acquired by the second camera.

Preferably, the defect of the web detected by the second image processor includes tear in the web and stain on the web.

Preferably, the sensor and the first camera are arranged so as to face an obverse side of the web on which the bands are formed, and the second camera is arranged so as to face a reverse side of the web.

Preferably, the mark is a label affixed to the web.

Preferably, the web is a web of wrapping paper for cigarettes.

Advantageous Effects of the Invention

According to the present invention, at least either defect in the bands or defect in the web can be detected by the detection unit, the type of the detected defect can be determined, and also the determination result can be managed. Thus, the inspection system can be maintained in accordance with the determination result, making it possible to improve productivity.

Also, according to the present invention, the determination section can determine not only the type of defect but also whether the detected defect of the band is a severe one or a minor one. The inspection system can therefore be adjusted quickly in accordance with the detected defect of the band.

Further, according to the present invention, the determination result provided by the determination section can be stored in the storage section, so that the determination result can be accumulated to serve for maintenance, enabling improvement in productivity as a result.

According to the present invention, moreover, the position of the defect in the web is stored and is also marked. This makes it possible to easily identify the position of the defect when the defect is removed in a subsequent process, thus improving productivity.

Furthermore, according to the present invention, presence and absence of each of the bands formed at predetermined intervals can be detected by the sensor and the rotary encoder. If a band is missing, it is judged that a severe defect has occurred. Such judgment is useful in maintaining the inspection system.

According to the present invention, the pulses output from the rotary encoder are counted and compared with the reference pulse count representative of the interval between adjacent ones of the bands. It is therefore possible to determine with accuracy whether or not the bands are formed at proper intervals.

Also, according to the present invention, if a severe defect occurs, traveling of the web is stopped, so that the coating device and the like can be promptly adjusted, making it possible to improve productivity.

Further, according to the present invention, an image of the web is acquired by the camera, and defect in the bands is detected from the acquired image, whereby a variety of defects that can occur in the bands can be detected.

Defect in the bands detected according to the present invention includes, for example, stain, uneven coating and pinhole that appear at random, periodically or continuously.

According to the present invention, the second detection device may additionally be provided to detect defect in the web, besides defect in the bands, whereby reliability of the product can be improved.

Such defect in the web can be detected by means of the camera and the image processor which is configured to process the image acquired by the camera.

Defect in the web detected according to the present invention includes, for example, tear in the web and stain on the web.

According to the present invention, the first detection device detects defects from the obverse side of the web and the second detection device detects defects from the reverse side of the web, whereby defects can be thoroughly detected.

Also, according to the present invention, a label may be used as the mark indicative of the position of the detected defect, and in this case, the invention can be easily implemented by using a label affixer.

Further, the web may be a web of wrapping paper for cigarettes. In this case, the inspection system of the present invention is suited for detection of defects in the bands formed by applying a combustion inhibitor as the coating liquid, as well as defects in the wrapping paper.

MODE FOR CARRYING OUT THE INVENTION

Figure 1:
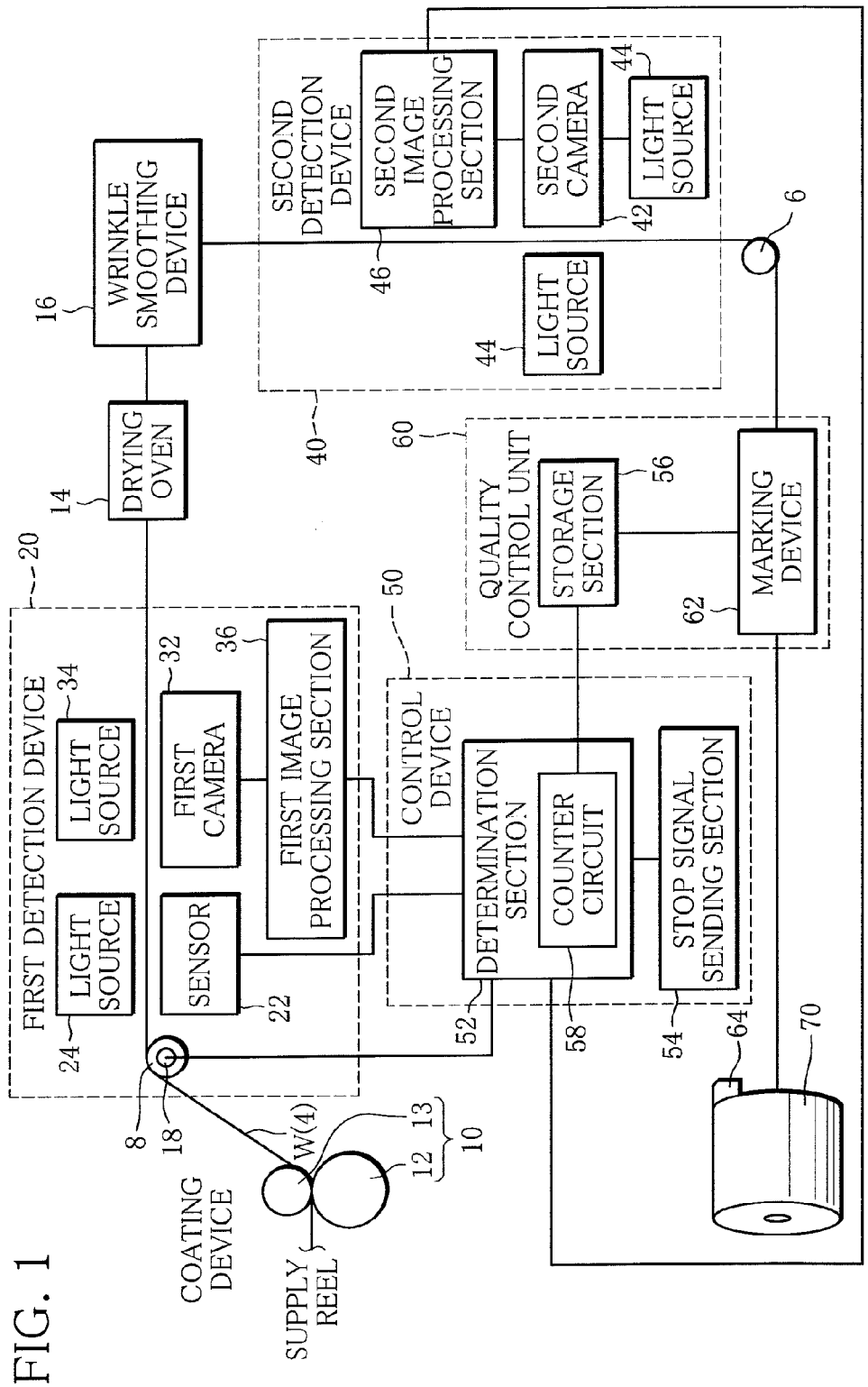
FIG. 1 schematically illustrates a coated paper inspection system according to the present invention.

Referring to FIG. 1, there is illustrated an inspection system 1 for carrying out a method according to the present invention. The inspection system 1 is provided with a traveling path 4 for a web W of wrapping paper for low ignition propensity cigarettes, and the traveling path 4 is formed by guide rollers 6, 8 and the like. The web W is unreeled from a supply reel toward a take-up reel (not shown) along the traveling path 4 and is wound onto the take-up reel.

Figure 2:
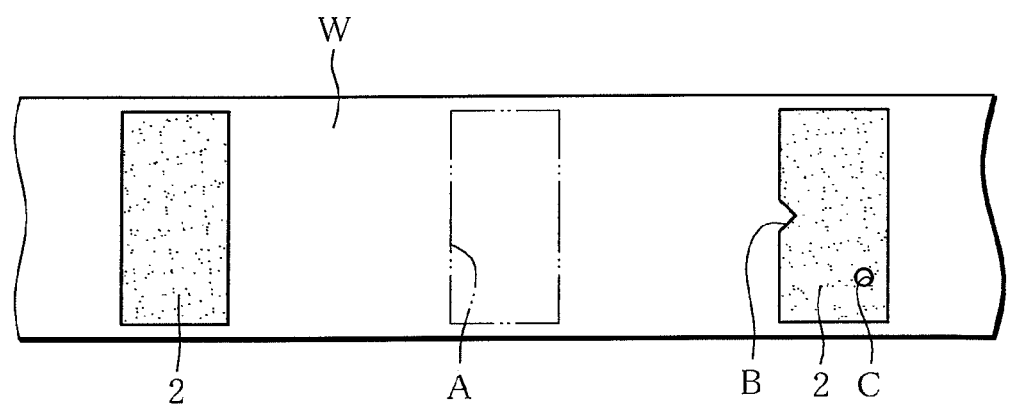
FIG. 2 schematically illustrates bands formed on a web.

A coating device 10 is arranged on an upstream side of the traveling path 4 and includes a gravure roller 12 and a pinch roller 13 so arranged as to nip the web W on the traveling path 4 therebetween. When the web W passes between the gravure roller 12 and the pinch roller 13, the gravure roller 12 applies a combustion inhibitor in liquid form as a coating liquid on one side, namely, on an obverse surface of the web W. The combustion inhibitor is applied to the web W at predetermined intervals in the traveling direction of the web W. Specifically, as shown in FIG. 2, numerous bands 2 of the combustion inhibitor are formed on the web W. The bands 2 extend over nearly the entire width of the web W and are spaced from each other in the traveling direction of the web W at the predetermined intervals.

A drying oven 14 as a drying device is disposed in the traveling path 4 at a location downstream of the coating device 10. The web W applied with the combustion inhibitor passes through the drying oven 14. The drying oven 14 has a plurality of hot air nozzles (not shown) arranged therein, and the hot air nozzles eject hot air into the drying oven 14. Thus, while the web W passes through the drying oven 14, the drying oven 14 dries the combustion inhibitor applied to the web W, namely, the bands 2.

Further, a wrinkle smoothing device 16 is disposed in the traveling path 4 at a location downstream of the drying oven 14, and the web W passes through the wrinkle smoothing device 16 after being dried. The wrinkle smoothing device 16 includes, for example, a pair of wrinkle smoothing rollers (not shown) so arranged as to nip the web W on the traveling path 4 therebetween and be movable toward each other into contact and away from each other. When the web W passes between the wrinkle smoothing rollers, the wrinkle smoothing rollers cooperate to press the web W therebetween. Thus, while the web W passes through the wrinkle smoothing device 16, the wrinkle smoothing device 16 smoothens wrinkles on the surfaces of the web W by means of the pressing force of the wrinkle smoothing rollers.

At the termination end of the traveling path 4, the aforementioned take-up reel is arranged to reel up the web W that has passed through the wrinkle smoothing device 16. As a result, a web roll 70 is formed. The web roll 70 is thereafter cut with a predetermined width.

When the combustion inhibitor is applied to the surface of the web W to form the bands 2 in the manner described above, a band defect may possibly occur at random or periodically or continuously. Such band defect includes, as shown in FIG. 2 by way of example, a lack A of the band 2 in its entirety, a lack B of part of the band 2, a pinhole C, a stain on the surface of the band 2, uneven coating and the like.

The guide roller 8 is disposed in the traveling path 4 at a location between the coating device 10 and the drying oven 14 and guides the web W downstream. A rotary encoder 18 is mounted on the rotary shaft of the guide roller 8 and is electrically connected to a determination section 52 of a control device 50, described later. The rotary encoder 18 successively outputs a pulse to the determination section 52 in accordance with an amount of rotational displacement of the rotary shaft of the guide roller 8, that is, in accordance with a feed rate of the web W.

Also, a first detection device 20 is disposed in the traveling path 4 at a location between the guide roller 8 and the drying oven 14. The first detection device 20 includes a sensor 22 and a light source 24 so arranged as to face each other with the web W on the traveling path 4 located therebetween. The sensor 22 is arranged on the same side as the obverse surface of the web W on which the bands 2 are formed, and is electrically connected to the determination section 52. The sensor 22 is capable of receiving signal light emitted from the light source 24 and detecting change in the amount of the received signal light. While the web W with the bands 2 is moving along the traveling path 4, the signal light can transmit through the band 2 but is blocked by the other region than the band 2, so that the amount of light received by the sensor 22 changes. The sensor 22 can therefore detect the presence and absence of each band 2, and the detection result is output as a pulse to the determination section 52. For the sensor 22, a transmission-type photoelectric sensor is preferably used, and the wavelength of the signal light is desirably in the range from visible radiation to near infrared radiation.

The determination section 52 includes a counter circuit 58 and is electrically connected with a stop signal sending section 54. The counter circuit 58 counts the pulses output from the rotary encoder 18. The number of pulses to be counted between adjacent ones of the bands 2 is stored beforehand as a reference pulse count in the determination section 52. If the number of pulses actually counted by the counter circuit exceeds the reference pulse count, the determination section 52 judges that the bands 2 are not normally formed at the predetermined intervals. In the example illustrated in FIG. 3, four pulses should be detected within the distance between adjacent ones of the bands 2, that is, in one band pitch P. Accordingly, the reference pulse count is "4". A value larger than the reference pulse count is set as a set count value (in the example of FIG. 3, "6"), and if the pulses are counted up to the set count value, it is judged that a band 2 that should be formed at the band pitch P is missing.

Figure 3:
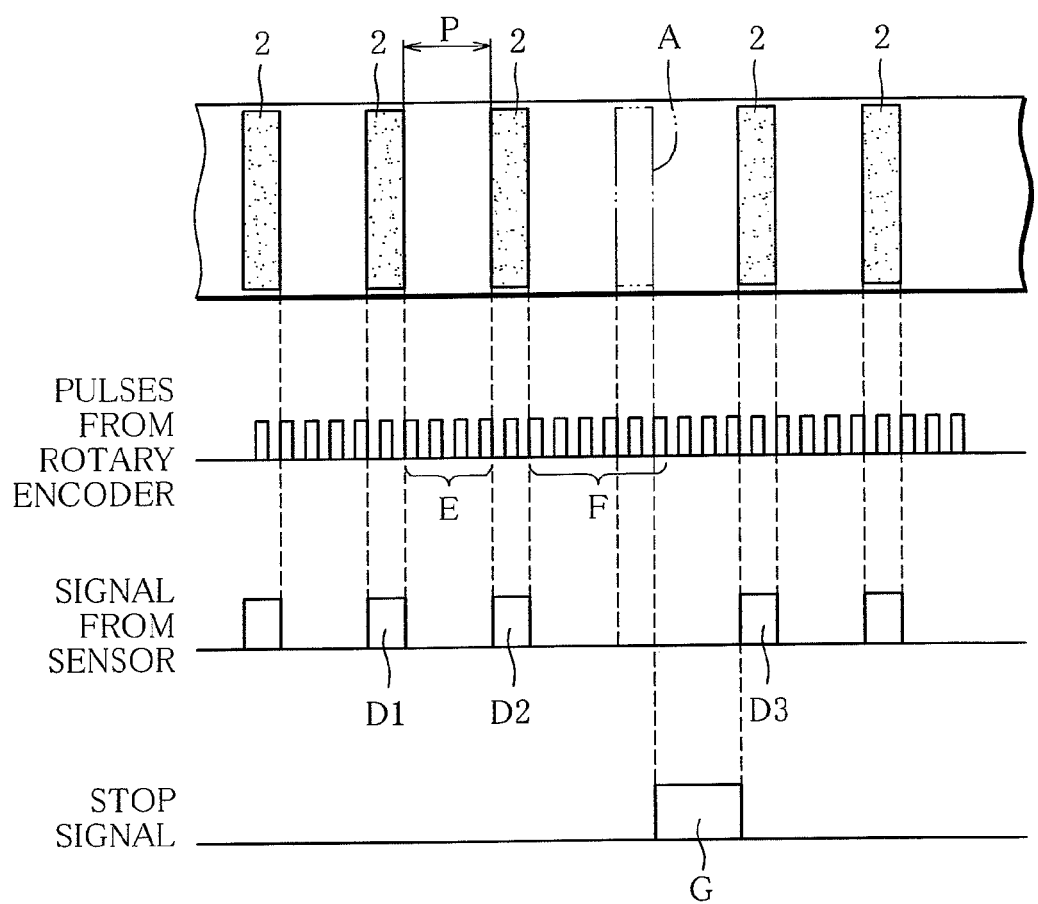
FIG. 3 is a conceptual diagram illustrating the manner of how the presence and absence of a band is detected by a first detection device.

To explain in more detail with reference to the example of FIG. 3, when a band 2 is detected by the sensor 22 (cf. FIG. 1), a signal D1 is input to the determination section 52 from the sensor 22. At the same time that the input of the signal D1 ends, the counter circuit starts counting the pulses E input from the rotary encoder 18 (cf. FIG. 1). When the next band 2 is detected thereafter, a signal D2 is input to the determination section 52 from the sensor 22. In the illustrated example, when the signal D2 is input, the number of pulses E counted until then is "4", which is equal to the reference pulse count. As soon as the signal D2 is input, the counter circuit resets the pulse count (to zero). Then, at the same time that the input of the signal D2 ends, the counter circuit again starts counting the pulses F. If the next band 2 fails to be detected, no signal is input to the determination section 52 from the sensor 22, and therefore, the counter circuit 58 keeps counting the pulses F. On counting a pulse corresponding to the set count value (in the illustrated example, "6"), the determination section 52 causes the stop signal sending section 54 to send out a stop signal G. Counting up to the set count value means that a band 2 that should be formed at the band pitch P is missing. Such lack of an entire band 2 is regarded as a severe defect, and the system is stopped.

As stated above, the sensor 22 of the first detection device 20 cooperates with the rotary encoder 18 to detect the presence and absence of each band 2 applied to the web W, that is, to determine whether or not the individual bands 2 have been properly formed at the predetermined intervals. Instead of stopping the system, the position of the detected defect may be stored and marked using a marking device, described later, so that the defective portion may be disposed of in a subsequent process. In this case, the presence and absence of the bands 2 can be continuously detected irrespective of whether a single band 2 or a plurality of consecutive bands 2 are missing. In the example of FIG. 3, the stop signal G is continuously output until a signal D3 indicative of detection of the next band 2 is input, and simultaneously with the input of the signal D3, the pulse count is reset. The presence and absence of the bands 2 is preferably detected immediately after the bands 2 are applied to the web W, that is, while the web W is still wet.

The first detection device 20 is further provided with a first camera 32 and a light source 34, which are arranged downstream of the sensor 22 and the light source 24 so as to face each other with the web W on the traveling path 4 located therebetween. The first camera 32 is a line scan camera, for example, and is arranged on the same side as the obverse surface of the web W on which the bands 2 are formed, so as to extend in the width direction of the web W. Thus, the first camera 32 is able to continuously image the surface of the web W over its entire width as the web W passes through the first detection device 20. Also, the first camera 32 is electrically connected to the determination section 52 via a first image processing section 36, and the image data acquired by the first camera 32 is processed by the first image processing section 36 and then output to the determination section 52.

Specifically, the first image processing section 36 subjects the image data acquired by the first camera 32 to subtraction processing. The subtraction process is performed by clipping the image data in the width direction of the web W and comparing the image data of adjacent bands 2 with each other. Thus, although the bands 2 are formed intermittently in the traveling direction of the web W, the first camera 32 and the first image processing section 36, that is, the first detection device 20 can detect band defects that occur at random, periodically or continuously. Lack of part of the band 2, pinhole, stain, uneven coating and the like can be detected as the band defects.

A second detection device 40 is disposed in the traveling path 4 at a location downstream of the wrinkle smoothing device 16. The second detection device 40 includes a second camera 42 and a pair of light sources 44. The second camera 42 is a line scan camera like the aforementioned first camera and is arranged on the side as the reverse surface of the web W on which no bands are formed. The two light sources 44 are arranged on both sides of the web W on the traveling path 4, respectively. Using the light emitted from the light sources 44 and transmitted through and reflected by the web W passing through the second detection device 40, the second camera 42 can continuously image the reverse surface of the web W over its entire width.

The second camera is electrically connected to the determination section 52 via a second image processing section 46. The image data acquired by the second camera 42 is processed by the second image processing section 46 and then output to the determination section 52. Like the first image processing section 36, the second image processing section 46 subjects the image data acquired by the second camera 42 to subtraction processing. Thus, the second camera 42 and the second image processing section 46, that is, the second detection device 40 can detect a tear in the web W, stain on the web W, and the like. After passing through the coating device 10, the web W is applied with the coating liquid and thus is wet; therefore, the web W is prone to tear while passing through the drying oven 14 and the wrinkle smoothing device 16. It is therefore desirable that the second detection device 40 be arranged downstream of the drying oven 14 and the wrinkle smoothing device 16.

Further, a quality control unit 60 is disposed in the traveling path 4 at a location downstream of the second detection device 40. The quality control unit 60 includes the marking device 62 and a storage section 56. The marking device 62 includes a label affixer which attaches a label 64 to the surface of the web W traveling along the traveling path 4. The label affixer is electrically connected with the storage section 56. The storage section 56, which is also electrically connected to the determination section 52, stores the results of determinations made by the determination section 52 on the basis of the detection results provided by the rotary encoder 18 and the first and second detection devices 20 and 40, that is, the positions and types of detected defects, as well as information indicating whether the individual defects are severe ones or minor ones. In accordance with the determination results stored in the storage section 56, the label affixer attaches the label 64 to the surface of the web W as a mark indicative of the presence of a defect. Thus, the label 64 serves as a mark identifying a particular position of the web W corresponding to a determination result provided by the determination section 52.

Figure 4:
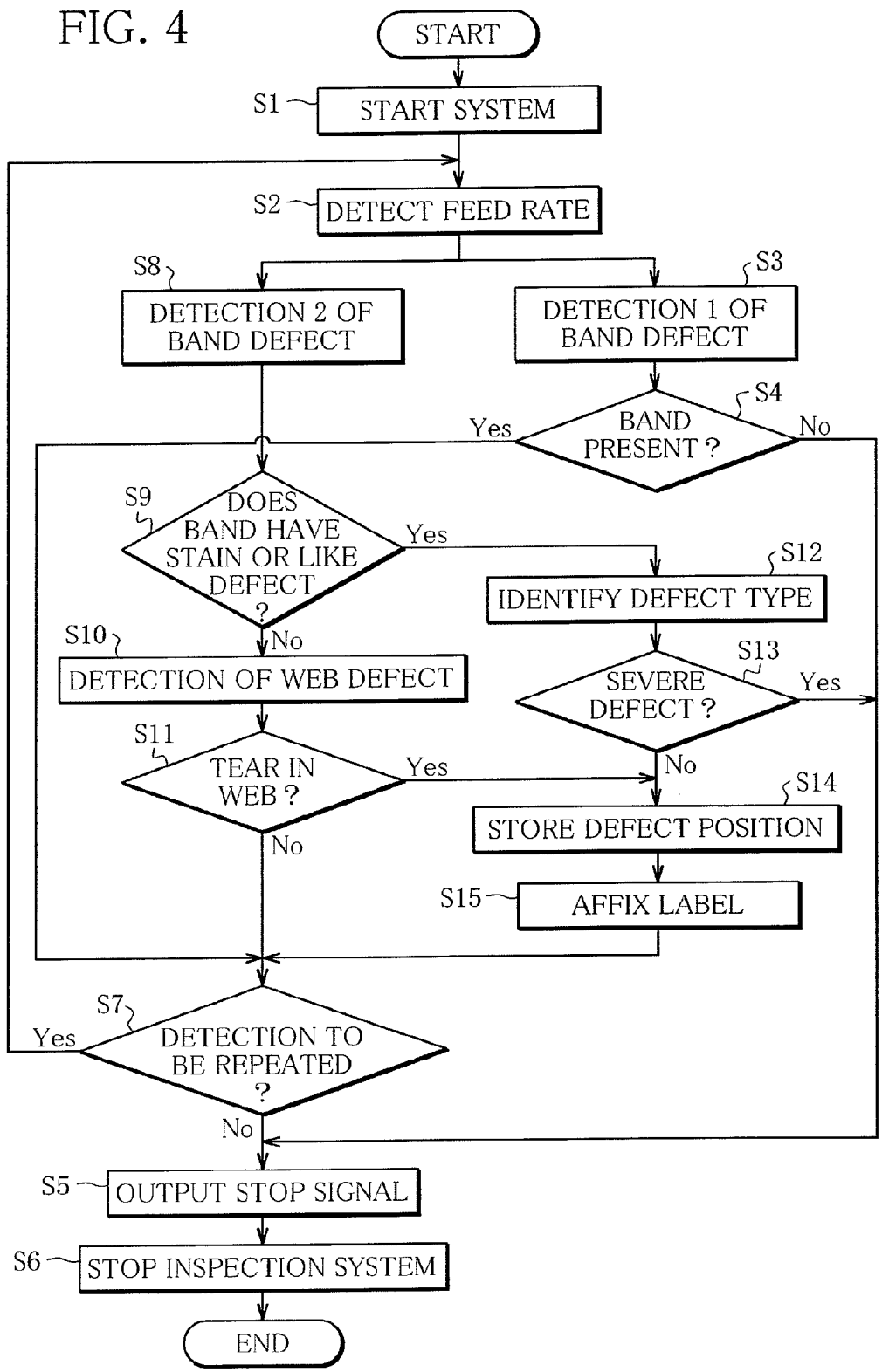
FIG. 4 is a flowchart illustrating a determination process executed by a control device.

The control device 50 will be now described in more detail with reference to the flowchart of FIG. 4. As mentioned above, the determination section 52 is electrically connected with the stop signal sending section 54 and the storage section 56.

First, the inspection system 1 is started [Step S1], and after the inspection system 1 is operated for preconditioning over a predetermined period, the feed rate of the web W is detected through the rotary encoder 18 [Step S2]. Then, a band defect is detected by the sensor 22 of the first detection device 20 [Step S3], and the determination section 52 determines whether or not every band 2 is formed on the web W [Step S4]. If the result of the determination is "False" (No), that is, if the detected band defect is judged to be a severe one, the judgment result is sent to the stop signal sending section 54. The stop signal sending section 54 sends out the stop signal to stop the inspection system 1 [Step S5], so that operation of the inspection system 1 is stopped [Step S6].

If the result of the determination in Step S4 is "True" (Yes), it is determined whether the aforementioned defect detection is to be repeated or not [Step S7], and if the result of the determination is "True" (Yes), Step S2 and the following steps are executed. If the result of the determination in Step S7 is "False" (No), the stop signal is output [Step S5], and the operation of the inspection system 1 is stopped [Step S6].

In parallel with the detection of the presence and absence of each band 2 in Step S3, defects such as a lack of part of the band 2 are detected through the first camera 32 of the first detection device 20 [Step S8], and the determination section 52 determines whether or not each band 2 is associated with such a defect [Step S9]. If the result of the determination is "False" (No), defects such as a tear in the web W are detected by the second detection device 40 [Step S10], and it is determined whether or not the web W is associated with such a defect [Step S11]. If the result of the determination is "False" (No), it is determined whether or not the aforementioned defect detection is to be repeated [Step S7], and if the result of the determination is "True" (Yes), Step S2 and the following steps are executed. If the result of the determination in Step S7 is "False" (No), the stop signal is output [Step S5], and the operation of the inspection system 1 is stopped [Step S6].

On the other hand, if the result of the determination in Step S9 is "True" (Yes), that is, if the band 2 has a defect, the type of defect is determined [Step S12], and then it is determined whether or not the detected defect is a severe one [Step S13]. If the result of the determination is "True" (Yes), that is, if the defect in the band 2 is a severe one, the stop signal is output [Step S5], and the operation of the inspection system 1 is stopped [Step S6]. If the result of the determination in Step S13 is "False" (No), that is, if the defect in the band 2 is a minor one, the defect position derived on the basis of the feed rate of the web W detected in Step S2 is stored in the storage section 56 [Step S14].

Also, if the result of the determination in Step S11 is "True" (Yes), that is, if the web W has a defect, the defect position derived on the basis of the feed rate of the web W detected in Step S2 is stored in the storage section 56 [Step S14].

Subsequently, the label 64 is affixed to the defect position of the web W stored in Step S14 [Step S15]. Further, it is determined whether or not the aforementioned defect detection is to be repeated [Step S7], and if the result of the determination is "True" (Yes), Step S2 and the following steps are executed. If the result of the determination in Step S7 is "False" (No), the stop signal is output [Step S5], and the operation of the inspection system 1 is stopped [Step S6].

As is clear from the above explanation, the inspection system 1 can detect the presence and absence of the individual bands 2 formed at the predetermined intervals, by means of the first detection device 20, namely, the sensor 22 and the rotary encoder 18. If the detection result indicates lack of a band 2, then it is judged by the determination section 52 of the control device 50 that a severe defect has occurred. In this case, the stop signal sending section 54 outputs the stop signal to stop traveling of the web W. The coating device 10 and the like can therefore be adjusted without delay, with the result that productivity improves.

The first camera 32 and the first image processing section 36 of the first detection device 20 are capable of detecting defects such as a lack of part of the band 2. Based on the detection result, the determination section 52 determines the type of the detected defect and also determines whether the defect is a severe one or a minor one. Consequently, various defects that can occur in the bands 2 can be detected.

If the detected defect is a minor one, the detection result is combined with the output from the rotary encoder 18, and the combined data is stored in the storage section 56 as the position of the defect. Then, the defect position is output to the label affixer, which affixes the label 64 to the defect position. Accordingly, when the defect is removed in a subsequent process, the defect position can be easily identified by the label 64, making it possible to improve the productivity of the coated paper. On the other hand, if the detected defect of the band 2 is a severe one, the web W is stopped traveling. Thus, the coating device 10 and the like can be adjusted without delay, so that productivity improves.

Further, the second camera 42 and the second image processing section 46 of the second detection device 40 can detect defects such as a tear in the web W and a stain on the web W, by imaging the web W and processing the acquired image data. The detection result is output to the determination section 52 and combined with the output from the rotary encoder 18, and the combined data is stored in the storage section 56 as the position of the defect in the web W. Subsequently, the defect position is output to the label affixer, which then affixes the label 64 to the defect position. Thus, not only defects in the bands 2 but also defects in the web W can be detected, and in addition, the positions of such defects can be easily identified, whereby the reliability of the coated paper can be improved.

The present invention is not limited to the foregoing embodiment and may be modified in various ways.

For example, the means for specifying the position of a defect in the band 2 or the web W is not limited to the label 64, and the defect position may be specified by coloring or the like. In this case, different colors may be used to indicate different types of defect.

Also, the inspection system of the present invention is suited for the inspection of not only the wrapping paper for low ignition propensity cigarettes but also coated paper such as packing paper or printing paper which is subjected to a coating process using a coating liquid, especially a coating process for coating part of the paper with a coating liquid.

EXPLANATION OF REFERENCE SIGNS

1: inspection system
2: band
4: traveling path
6: guide roller
8: guide roller
10: coating device
12: gravure roller
13: pinch roller
14: drying oven (drying device)
16: wrinkle smoothing device
18: rotary encoder
19: detection unit
20: first detection device
22: sensor
24: light source
32: first camera
34: light source
36: first image processing section (first image processor)
40: second detection device
42: second camera
44: light source
46: second image processing section (second image processor)
50: control device
52: determination section
54: stop signal sending section
56: storage section
58: counter circuit
60: quality control unit
62: marking device
64: label
70: roll
W: web

The invention claimed is:

1. An inspection system for coated paper, comprising:
a traveling path along which a web of paper travels;
a coating device configured to form a plurality of bands on the web by applying a coating liquid in a width direction of the web such that the bands are spaced from each other in a longitudinal direction of the web at regular intervals;
a drying device configured to dry the web having the bands formed thereon;
a detection unit arranged downstream of said coating device and configured to detect at least either defect in any one of the bands or defect in the web that is caused due to application of the coating liquid to the web;
a control device input with a detection result from said detection unit and including a determination section configured to determine a type of the defect from the detection result; and
a quality control unit input with a determination result from the determination section and configured to manage the determination result;
wherein said detection unit includes a first detection device arranged upstream of said drying device and configured to detect defect in any one of the bands;
the first detection device includes a sensor configured to detect presence and absence of each of the bands, and a rotary encoder configured to output a signal at every inspection time when each of the bands is to pass the sensor; and
the determination section judges that a severe defect has occurred if it is found based on outputs from the sensor and the rotary encoder that the bands are not formed at the regular intervals.

2. The inspection system according to claim 1, wherein said quality control unit includes a storage section configured to store the determination result.

3. The inspection system according to claim 2, wherein:
the determination section determines a position of the defect of the band or the web with respect to the web and outputs a determination result to the storage section, and
said quality control unit further includes a marking device arranged downstream of said drying device and configured to affix, on the web, a mark indicative of presence of the defect of the band or the web in accordance with the position of the defect stored in the storage section.

4. The inspection system according to claim 1, wherein:
the determination section includes a counter circuit configured to count pulses output from the rotary encoder, and
the determination section stores, in advance as a reference pulse count, a number of the pulses to be counted between adjacent ones of the bands, and judges that the bands are not formed at the regular intervals if the reference pulse count is exceeded by a number of actually counted pulses.

5. The inspection system according to claim 1, wherein said control device further includes a stop signal sending section configured to output an instruction to stop traveling of the web when it is judged by the determination section that the severe defect has occurred.

6. The inspection system according to claim 1, wherein the first detection device further includes a first camera configured to image the web having the bands formed thereon, and a first image processor configured to detect defect in any one of the bands from an image acquired by the first camera.

7. The inspection system according to claim 6, wherein the defect of the band detected by the first image processor includes stain, uneven coating and pinhole that appear at random, periodically or continuously.

8. The inspection system according to claim 3, wherein:
said detection unit includes a second detection device arranged downstream of said drying device and upstream of the marking device and configured to detect defect in the web, and
the determination section is input with a detection result from the second detection device.

9. The inspection system according to claim 8, wherein the second detection device includes a second camera configured to image the web, and a second image processor configured to detect defect in the web from an image acquired by the second camera.

10. The inspection system according to claim 9, wherein the defect of the web detected by the second image processor includes tear in the web and stain on the web.

11. The inspection system according to claim 9, wherein:
the sensor and the first camera are arranged so as to face an obverse side of the web on which the bands are formed, and
the second camera is arranged so as to face a reverse side of the web.

12. The inspection system according to claim 4, wherein the mark is a label affixed to the web.

13. The inspection system according to claim 1, wherein the web is a web of wrapping paper for cigarettes.

14. An inspection system for coated paper, comprising:
a traveling path along which a web of paper travels;
a coating device configured to form a plurality of bands on the web by applying a coating liquid in a width direction of the web such that the bands are spaced from each other in a longitudinal direction of the web at regular intervals;
a drying device configured to dry the web having the bands formed thereon;
a detection unit arranged downstream of said coating device and configured to detect at least either defect in any one of the bands or defect in the web that is caused due to application of the coating liquid to the web;
a control device input with a detection result from said detection unit and including a determination section configured to determine a type of the defect from the detection result, wherein the determination section determines whether the defect of the band is a severe one or a minor one; and
a quality control unit input with a determination result from the determination section and configured to manage the determination result;
wherein said detection unit includes a first detection device arranged upstream of said drying device and configured to detect defect in any one of the bands;
the first detection device includes a sensor configured to detect presence and absence of each of the bands, and a rotary encoder configured to output a signal at every inspection time when each of the bands is to pass the sensor; and
the determination section judges that a severe defect has occurred if it is found based on outputs from the sensor and the rotary encoder that the bands are not formed at the regular intervals.

\* \* \* \* \*